US010918311B2

(12) United States Patent
Kim et al.

(10) Patent No.: US 10,918,311 B2
(45) Date of Patent: Feb. 16, 2021

(54) USER MOVEMENT MONITORING METHOD AND SYSTEM PERFORMING THE SAME

(71) Applicant: KOREA ELECTRONICS TECHNOLOGY INSTITUTE, Seongnam-si (KR)

(72) Inventors: Kunnyun Kim, Yongin-si (KR); Kwang Bum Park, Yongin-si (KR); Won Hyo Kim, Yongin-si (KR); Yeon Hwa Kwak, Seoul (KR)

(73) Assignee: Korea Electronics Technology Institute, Seongnam-si (KR)

( * ) Notice: Subject to any disclaimer, the term of this patent is extended or adjusted under 35 U.S.C. 154(b) by 364 days.

(21) Appl. No.: 15/891,299

(22) Filed: Feb. 7, 2018

(65) Prior Publication Data

US 2018/0160940 A1 Jun. 14, 2018

Related U.S. Application Data

(63) Continuation of application No. PCT/KR2016/001249, filed on Feb. 4, 2016.

(30) Foreign Application Priority Data

Aug. 7, 2015 (KR) .................... 10-2015-0111694

(51) Int. Cl.
*A61B 5/11* (2006.01)
*G06K 9/00* (2006.01)
(Continued)

(52) U.S. Cl.
CPC ............... *A61B 5/11* (2013.01); *A61B 5/1116* (2013.01); *A61B 5/45* (2013.01); *G06F 3/016* (2013.01);
(Continued)

(58) Field of Classification Search
CPC ......... A61B 5/11; A61B 5/1107; A61B 5/114; A61B 5/116; A61B 5/118;
(Continued)

(56) References Cited

U.S. PATENT DOCUMENTS

2010/0188231 A1* 7/2010 Winter .................... A61B 5/00 340/573.1
2012/0071743 A1 3/2012 Todorov et al.
(Continued)

FOREIGN PATENT DOCUMENTS

KR 10-2007-0061476 A 6/2007
KR 10-2014-0078704 A 6/2014
(Continued)

OTHER PUBLICATIONS

International Search Report dated May 30, 2016 of PCT/KR2016/001249 which is the parent application and its English translation—10 pages.

*Primary Examiner* — Thaddeus B Cox
(74) *Attorney, Agent, or Firm* — Knobbe Martens Olson & Bear LLP

(57) ABSTRACT

Provided are a method and a system for monitoring a movement of a user. The system includes at least one wearable flexible tactile sensor configured to sense movement of a muscle or bending of a joint at a corresponding location and transmitting a sensed value. The system further includes a monitoring server configured to analyze movement of the muscle or the bending of the joint of the user based on the sensed value received from the flexible tactile sensor motility of the user.

9 Claims, 13 Drawing Sheets

(51) Int. Cl.
  *A61B 5/00* (2006.01)
  *G06F 3/01* (2006.01)
  *G08B 6/00* (2006.01)

(52) U.S. Cl.
  CPC .. *G06K 9/00496* (2013.01); *A61B 2562/0261* (2013.01); *G06K 9/00342* (2013.01); *G06K 9/00355* (2013.01); *G08B 6/00* (2013.01)

(58) Field of Classification Search
  CPC ....... A61B 5/1121–1123; A61B 5/1126; A61B 2562/0261; G06K 9/00342–00348
  See application file for complete search history.

(56) References Cited

U.S. PATENT DOCUMENTS

| | | |
|---|---|---|
| 2012/0245482 A1 | 9/2012 | Bolser et al. |
| 2014/0171838 A1 | 6/2014 | Aleksov et al. |

FOREIGN PATENT DOCUMENTS

| | | |
|---|---|---|
| KR | 10-2015-0043531 A | 4/2015 |
| KR | 10-2015-0047171 A | 5/2015 |

\* cited by examiner

SETTING SENSOR WEARING LOCATION

| SENSOR NUMBER | REGION | LOCATION |
|---|---|---|
| 1 | FIRST SENSOR | NECK | LOWER NECK CIRCUMFERENCE |
| 2 | SECOND SENSOR | ARM | LOWER PART OF WRIST |
| 3 | THIRD SENSOR | LEG | THIGH |
| 4 | FOURTH SENSOR | BACK | VICINITY OF WAIST |
| ⋮ | ⋮ | ⋮ | ⋮ |

FIG.3

USER MOVEMENT MONITORING METHOD AND SYSTEM PERFORMING THE SAME

CROSS-REFERENCE TO RELATED APPLICATIONS

This application is a continuation application, and claims the benefit under 35 U.S.C. §§ 120 and 365 of PCT Application No. PCT/KR2016/001249, filed on Feb. 4, 2016, which is hereby incorporated by reference. PCT/KR2016/001249 also claimed priority from Korean Patent Application No. 10-2015-0111694 filed on Aug. 7, 2015, which is hereby incorporated by reference.

BACKGROUND

Field

The present disclosure relates to a technique for monitoring a movement of a user, and more particularly, to a method and a system for monitoring a movement of a user, which can accurately sense a movement of a muscle of the user or bending of a joint by using a flexible tactile sensor and monitor a remedial exercise of the user or correcting an exercise posture of the user by using the sensed movement and bending.

Related Art

In the related art, an exercise consulting providing method is achieved by acquiring user information including body information such as a weight, a height, blood glucose, etc., of a user and profile information such as a name, an occupation, an address, a hobby, etc., comparing the acquired user information and rule information stored in a rule database, and providing a rule which matches the user information, that is, exercise consulting information even to the user.

However, a method for providing exercise consulting information in the related art has a problem in which since vast exercise consulting data cannot be accurately used and further, it is difficult to provide personalized exercise consulting information to a large number of users due to a shortage of an expert consultant.

Korean Patent Unexamined Publication No. 10-2015-0047171 relates to an apparatus and a method for monitoring an exercise and discloses an exercise monitoring technique which can provide motivation for the exercise so as to maintain a regular exercise program and form a social network having high concentration and loyalty. To this end, the exercise monitoring apparatus includes a receiving unit for receiving exercise data measured by an exercise assisting apparatus worn on a part of a body of a user; an exercise amount setting unit for setting a daily target exercise amount of the user; and a compensation control unit for awarding compensation symbols and mileage to the user when a daily exercise amount of the user is equal to or greater than the daily target exercise amount.

Korean Patent Unexamined Publication No. 10-2015-0043531 relates to fitness monitoring using a mobile device and an exercise monitoring device may include or be associated with multiple types of mobile sensors and switches and sensors may be switched according to various factors including an exercise pattern or both sensors may be used. The exercise may also be tagged with various parameters including mood, weather, terrain, exercise equipment used, etc., and the parameters may be automatically determined based on a position. User exercises and accomplishments can also be celebrated through messages from celebrities, family, friends, and other users. Coaching can be provided to the user to help improve exercise and overall exercise performance.

The present disclosure is made in association with a Korean national research and development project (research project name: Development of precise motion tracking and pressure sensing technology with flexible/ultra thin/light weight strain and force sensors for finger motion tracking, project identification number: 10079763).

The disclosure of this section is to provide background of the described technology. Applicant notes that this section may contain information available before this application. However, by providing this section, Applicant does not admit that any information contained in this section constitutes prior art.

SUMMARY

An aspect of the present invention provides a user movement monitoring method which can monitor a movement of a user through a flexible tactile sensor capable of sensing force both planes and a system performing the same.

An aspect of the present invention also provides a user movement monitoring method which can accurately sense and monitor the movement of a muscle or bending of a joint depending on an exercise of the user by using the flexible tactile sensor which can be worn on a body of the user and a system performing the same.

An aspect of the present invention also provides a method and a system for monitoring a movement of a user which can sense the movement of the muscle of the user or the bending of the joint and monitor a remedial exercise of the user or an exercise posture of the user by using the sensed movement of the muscle or bending of the joint.

Another aspect, of the present invention provides a system for monitoring a movement of a user which includes: at least one flexible tactile sensor worn on a body of the user and sensing the movement of a muscle or bending of a joint at a corresponding location and transmitting a sensed value; and a monitoring server analyzing the movement of the muscle or the bending of the joint of the user based on the sensing value received from the flexible tactile sensor and monitoring motility of the user.

In an embodiment, the system may further include a mobile terminal wirelessly connected with the at least one flexible tactile sensor, and the mobile terminal may transmit the sensing value received from the at least one flexible tactile sensor to the monitoring server.

In an embodiment, when the at least one flexible tactile sensor is worn on the body of the user, the mobile terminal may receive and store an initial sensing value of each flexible tactile sensor.

In an embodiment, the mobile terminal may include a table storing an identification number of the at least one flexible tactile sensor and a wearing location of a corresponding sensor in the body of the user.

In an embodiment, the mobile terminal may transmit the wearing location of the at least one flexible tactile sensor, the initial sensing value of each flexible tactile sensor, and the sensing value of each flexible tactile sensor depending on the movement of the user to the monitoring server.

In an embodiment, the flexible tactile sensor may include a tactile sensor array constituted by a plurality of tactile sensor modules.

In an embodiment, the tactile sensor module may include a polymer layer, a first metal layer formed on the top of the polymer layer, a first sensor layer including a strain gauge formed on the top of the first metal layer and having a resistance value which varies depending on strain and a metal wire connected to the strain gauge, a first cover layer protecting the first sensor layer, a second metal layer formed on the bottom of the polymer layer, a second sensor layer including the strain gauge formed on the bottom of the second metal layer and having a resistance value which varies depending on strain and the metal wire connected to the strain gauge, and a second cover layer protecting the second sensor layer.

In an embodiment, the first sensor layer may include a first strain gauge, a first metal wire connected to each of one end and the other end of the first strain gauge, a second drain gauge, and a second metal wire connected to each of one end and the other end of the second strain gauge.

In an embodiment, the first strain gauge and the second strain gauge may be formed such that longitudinal axes of the first and second strain gauges have a predetermined angle with a vertical axis of a plane.

In an embodiment, the first strain gauge and the second strain gauge may be formed such that lengths of line widths of the stain gauges and lengths of gaps between lines are different from each other.

In an embodiment, the flexible tactile sensor may be worn at a location corresponding to the muscle or joint associated with a remedial exercise of the user and the monitoring server may monitor a remedial exercise result of the user based on the received sensing value.

In an embodiment, the monitoring server may monitor an improvement degree of the muscle or a function improvement degree of the joint of the user depending on the remedial exercise.

In an embodiment, the flexible tactile sensor may be worn at a location corresponding to the muscle or joint associated with a training exercise of the user and the monitoring server may monitor a training exercise result of the user based on the received sensing value.

In an embodiment, the monitoring server may compare and monitor a reference posture of the training exercise and the posture of the user depending on the movement of the muscle or the bending of the joint of the user.

In another aspect, the present invention provides a method for monitoring a movement of a user which includes: sensing, by at least one flexible tactile sensor worn on a body of the user, the movement of a muscle or bending of a joint at a corresponding location and transmitting a sensed value to a mobile terminal; transmitting, by the mobile terminal, the sensing value received from the at least one flexible tactile sensor to a monitoring server; and analyzing, by the monitoring server, the movement of the muscle or the bending of the joint of the user based on the received sensing value and monitoring motility of the user.

In an embodiment, the method for monitoring a movement of a user may further include setting, by the mobile terminal, a wearing location of the flexible tactile sensor in the body of the user.

In an embodiment, the method for monitoring a movement of a user may further include: receiving and storing an initial sensing value from the flexible tactile sensor; and transmitting the wearing location and the initial sensing value of the flexible tactile sensor.

In an embodiment, in the monitoring of the motility of the user, the movement of the user may be analyzed based on the wearing location of the flexible tactile sensor, the initial sensing value, and the sensing value depending on the movement of the user.

In an embodiment, the method for monitoring a movement of a user may further include providing, by the monitoring server, monitoring result information to the mobile terminal.

In an embodiment, the method for monitoring a movement of a user may further include providing, by the monitoring server, the monitoring result information to a medical team terminal.

A method and a system for monitoring a movement of a user according to an embodiment of the present invention can monitor the movement of the user through a flexible tactile sensor capable of sensing force both planes.

The method and the system for monitoring a movement of user according to an embodiment of the present invention can accurately sense and monitor the movement of a muscle or bending of a joint depending on an exercise of the user by using the flexible tactile sensor which can be worn on a body of the user.

The method and the system for monitoring a movement of user according to an embodiment of the present invention can sense the movement of the muscle of the user or the bending of the joint and monitor a remedial exercise of the user or an exercise posture of the user by using the sensed movement of the muscle or bending of the joint.

BRIEF DESCRIPTION OF THE DRAWINGS

FIG. 3 is a diagram schematizing a first example of setting a wearing location of the flexible tactile sensor in a mobile terminal illustrated in FIG. 1.

DESCRIPTION OF EMBODIMENTS

Figure 1:
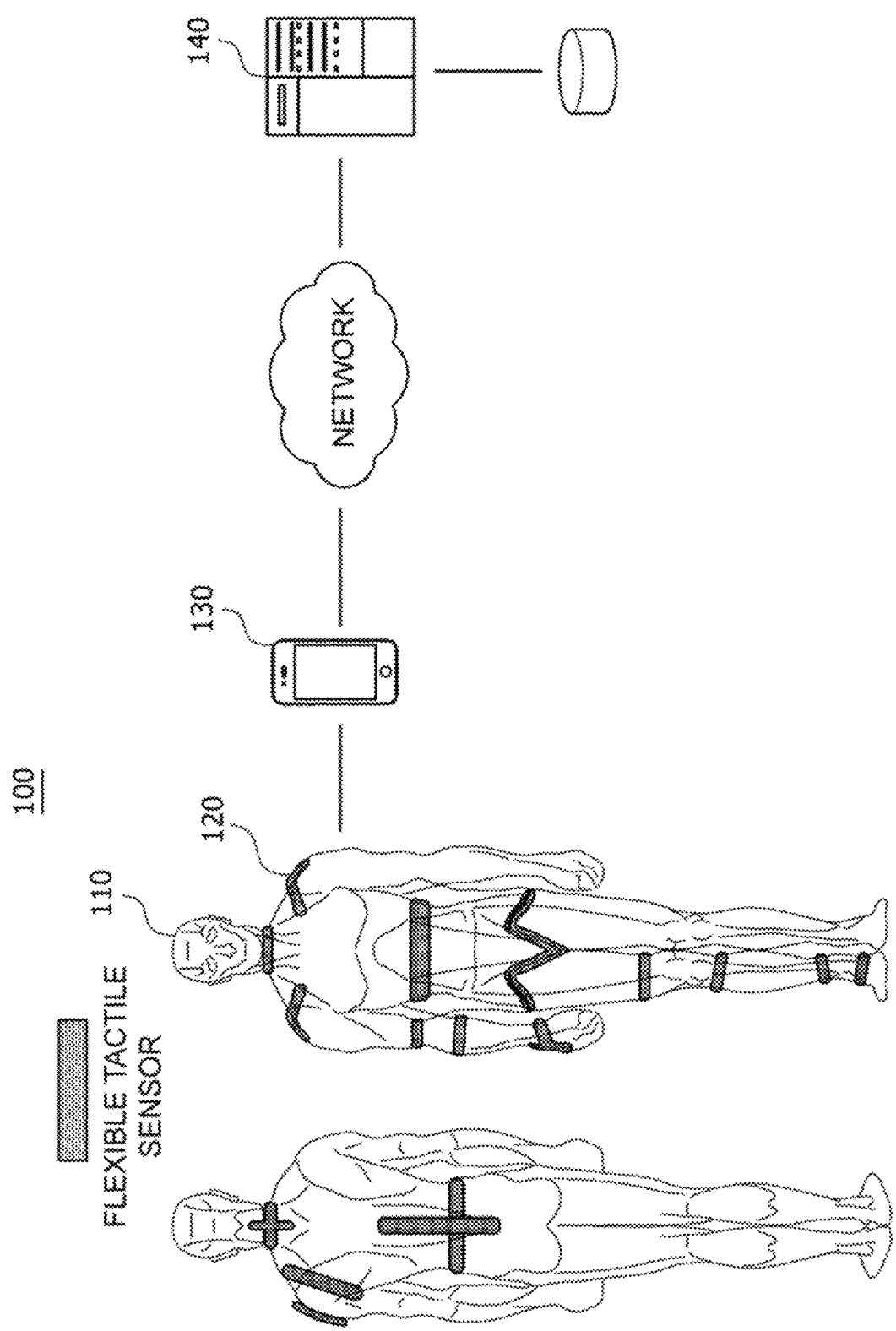
FIG. 1 is a diagram for describing a system for monitoring a movement of a user according to an embodiment of the present invention.

The scope of the present invention is not limited to the disclosed embodiments. That is, since embodiments of the invention can be variously changed and have various forms, the scope of the present invention should be understood to include equivalents capable of realizing the technical spirit. Further, it should be understood that since a specific embodiment should include all objects or effects or include only the effect, the scope of the present invention is limited by the object or effect.

Meanwhile, meanings of terms described in the present application should be understood as follows.

The terms "first," "second,", and the like are used to differentiate a certain component from other components, but the scope of should not be construed to be limited by the terms. For example, a first component may be referred to as a second component, and similarly, the second component may be referred to as the first component.

It should be understood that, when it is described that a component is "connected to" another component, the component may be directly connected to another component or a third component may be present therebetween. In contrast, it should be understood that, when it is described that an element is "directly connected to" another element, it is understood that no element is present between the element and another element. Meanwhile, other expressions describing the relationship of the components, that is, expressions such as "between" and "directly between" or "adjacent to" and "directly adjacent to" should be similarly interpreted.

It is to be understood that the singular expression encompass a plurality of expressions unless the context clearly dictates otherwise and it should be understood that term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

In each step, reference numerals (e.g., a, b, c, etc.) are used for convenience of description, the reference numerals are not used to describe the order of the steps and unless otherwise stated, it may occur differently from the order specified. That is, the respective steps may be performed similarly to the specified order, performed substantially simultaneously, and performed in an opposite order.

The present invention can be implemented as a computer-readable code on a computer-readable recording medium and the computer-readable recording medium includes all types of recording devices for storing data that can be read by a computer system. Examples of the computer readable recording medium include a ROM, a RAM, a CD-ROM, a magnetic tape, a floppy disk, an optical data storage device, and the like and further include a device implemented as a type of a carrier wave (e.g., transmission through the Internet). Further, the computer readable recording media may be stored and executed as codes which may be distributed in the computer system connected through a network and read by a computer in a distribution method.

If it is not contrarily defined, all terms used herein have the same meanings as those generally understood by those skilled in the art. Terms which are defined in a generally used dictionary should be interpreted to have the same meaning as the meaning in the context of the related art, and are not interpreted as an ideal meaning or excessively formal meanings unless clearly defined in the present application.

FIG. 1 is a diagram for describing a system for monitoring a movement of a user according to an embodiment of the present invention.

Referring to FIG. 1, the system for monitoring a movement of a user includes a flexible tactile sensor 120, a mobile terminal 130, and a monitoring server 140. The flexible tactile sensor 120 is worn on a body of a user 110 and senses the movement of a muscle or the bending of the joint at a position where the sensor is worn. The flexible tactile sensor 120 senses force on both planes to accurately sense the movement of the muscle or bending of the joint.

In an embodiment, the flexible tactile sensor 120 may include a detachment/attachment portion on one surface and may be detached from/attached to the body of the user 110 through the detachment/attachment portion. In another embodiment, flexible tactile sensor 120 is provided on a garment, wearable exercise aids (e.g., arm warmers, waist support, gloves, posture corrector, etc.), and the like which the user 110 may wear to be worn on the body of the user 110.

At least one flexible tactile sensor 120 may be worn on the body of the user 110. For example, the flexible tactile sensor 120 may be worn at a location corresponding to the muscle or joint associated with the remedial exercise or training.

Figure 2A:
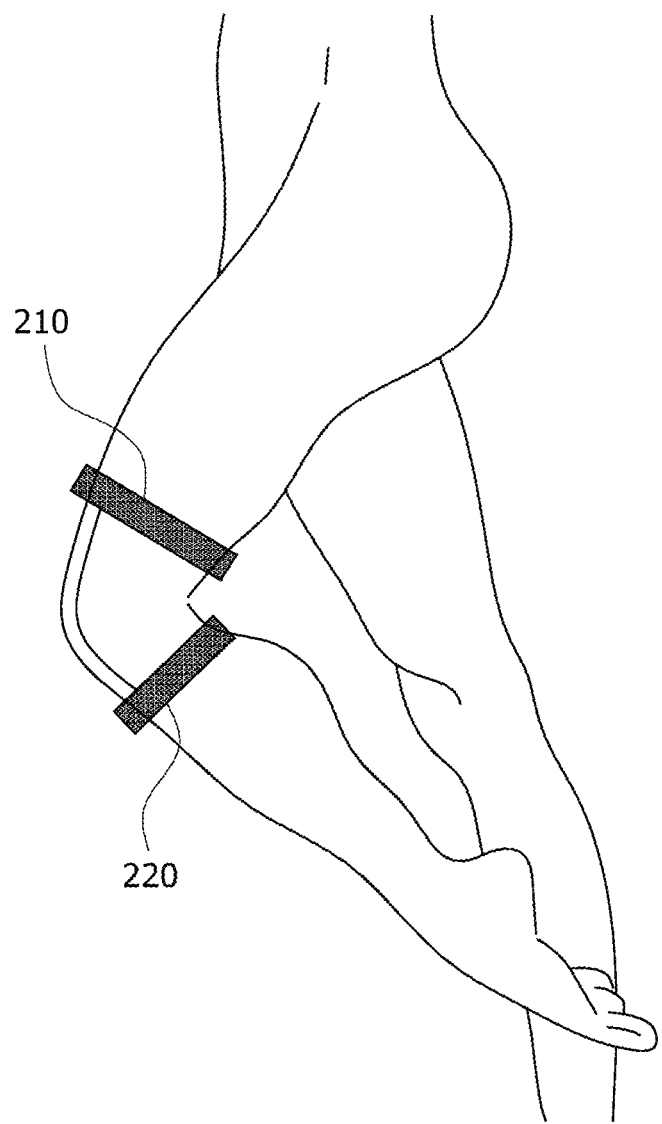
FIGS. 2A and 2B are diagrams illustrating an example in which a flexible tactile sensor is worn on a body.
Figure 2B:
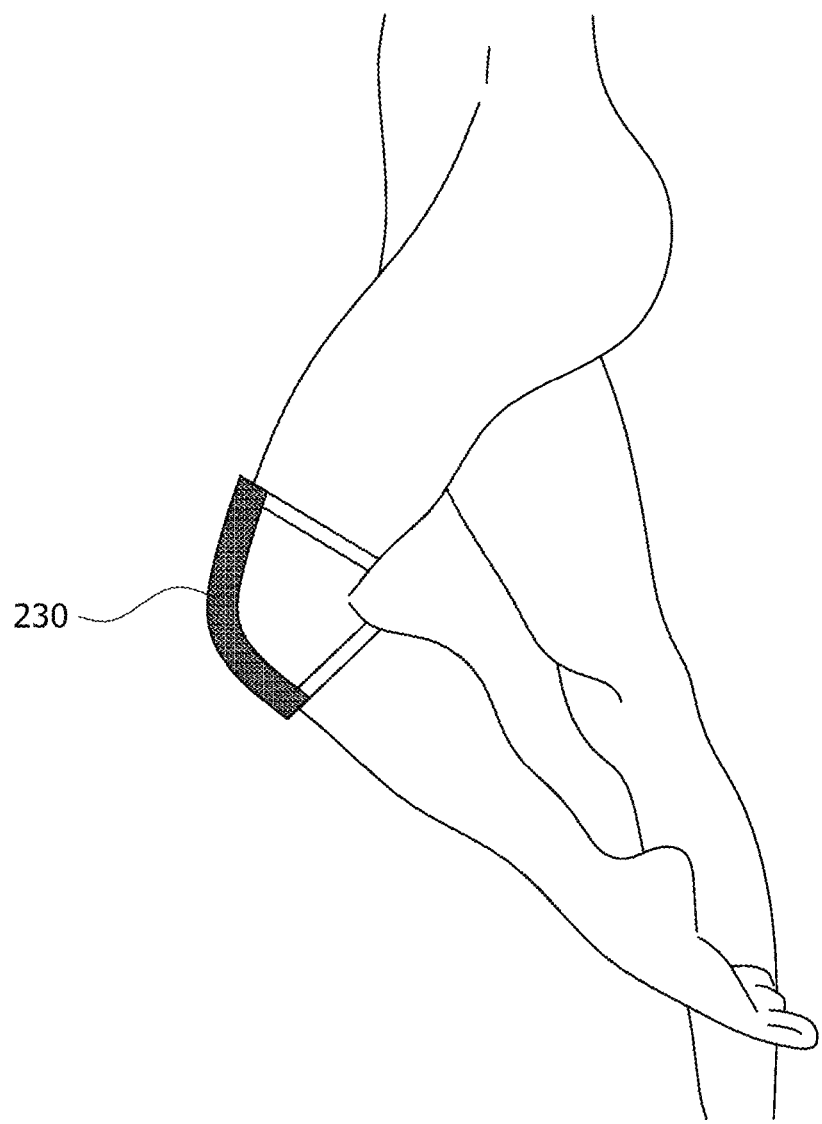

FIGS. 2A and 2B are diagrams illustrating an example in which a flexible tactile sensor is worn on a body.

When the flexible tactile sensor 120 is worn at a position corresponding to a specific muscle, the flexible tactile sensor 120 may measure the movement of the muscle. For example, in FIG. 2A, a first flexible tactile sensor 210 is worn on the femur (thigh) to measure the movement of the femur muscle and a second flexible tactile sensor 220 is worn on a shin to measure the movement of a shin muscle.

When the flexible tactile sensor 120 is worn at a position corresponding to the joint, the flexible tactile sensor 120 may measure the bending of the joint. For example, in FIG. 2B, a third flexible tactile sensor 230 is worn on a knee to measure the bending of the knee.

The flexible tactile sensor 120 may be worn on the body of the user 110 in various forms according to requirements. For example, the position, the number, and a shape of the flexible tactile sensor 120 may be determined depending on conditions such as a monitoring purpose, a user's physical condition, and a type of the muscle or joint.

Referring back to FIG. 1, the flexible tactile sensor 120 transmits a value sensed at a corresponding position to the mobile terminal 130. The mobile terminal 130 may be connected to at least one flexible tactile sensor 120 wirelessly or by wire. For example, the mobile terminal 130 may be connected to at least one flexible tactile sensor 120 using wireless communication means such as Bluetooth and short-range wireless communication. The mobile terminal 130 may include a smart phone, a tablet PC, a wearable PC, or a laptop PC.

In an embodiment, the mobile terminal 130 may include a user movement monitoring application and may perform a user movement monitoring process through the application. Prior to performing the user movement monitoring process, the mobile terminal 130 may perform initial setting and initial value measurement procedures under the control of the user.

The mobile terminal 130 may set a wearing location of the flexible tactile sensor 120 worn by the body of the user 110. For example, the mobile terminal 130 may set the wearing location of the flexible tactile sensor 120 through the user movement monitoring application, match the sensing value received by the sensor with the position of the sensor, and transmit the sensed value to the monitoring server 140.

FIG. 3 is a diagram schematizing a first example of setting a wearing location of the flexible tactile sensor in a mobile terminal illustrated in FIG. 1.

Referring to FIG. 3, the mobile terminal 130 may provide a first interface 310 for setting the wearing location of the flexible tactile sensor 120. FIG. 3 is an example of an interface which may receive the wearing location as a text from the user and set the wearing location or receive the wearing location through a selection menu and set the wearing location.

The first interface 310 includes a sensor number setting unit 320, a wearing region setting unit 330, and a detailed location setting unit 340. Each of the setting units 320, 330, and 340 may be implemented with an input window or a selection button.

The sensor number setting unit 320 may display an identification number of at least one flexible tactile sensor 120 worn on the body of the user 110. In an embodiment, the sensor number setting unit 320 may display the identification number of the flexible tactile sensor 120, which is set by a setting command of the user. In another embodiment, the identification number of the flexible tactile sensor 120 sensed by the mobile terminal 130 may be automatically displayed in the sensor number setting unit 320.

The wearing region setting unit 330 and the detailed location setting unit 340 may set a region where the flexible tactile sensor 120 is worn and a detailed location at the corresponding region by the setting command of the user.

For example, in FIG. 3, it can be seen that a first sensor is worn on a neck region and the first sensor is worn on a lower neck circumference even at the neck region. Further, it can be seen that a third sensor is worn on a leg and the third sensor is worn on the thigh even at the leg.

Figure 4:
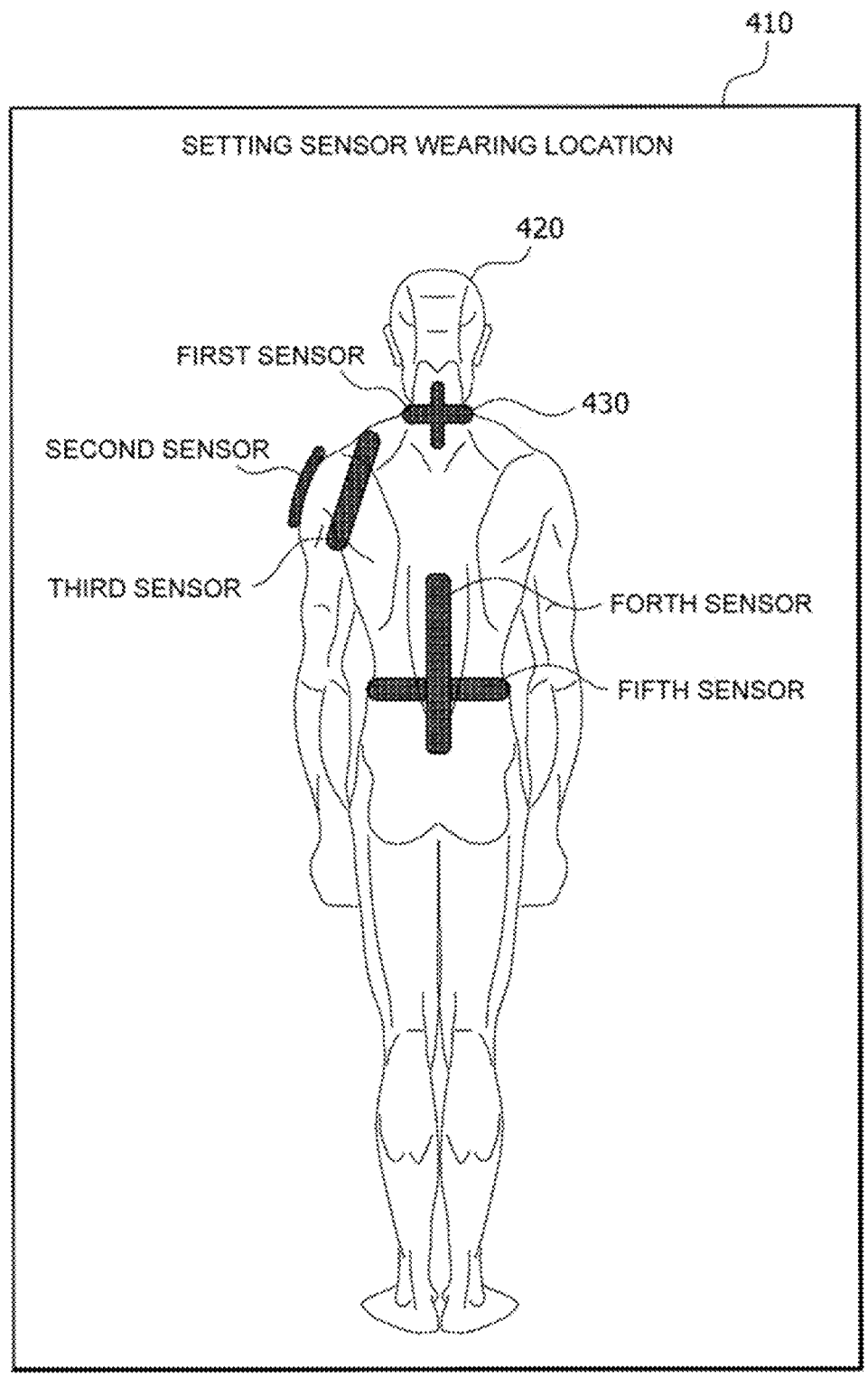
FIG. 4 is a diagram schematizing a second example of setting the wearing location of the flexible tactile sensor in the mobile terminal illustrated in FIG. 1.

FIG. 4 is a diagram schematizing a second example of setting the wearing location of the flexible tactile sensor in the mobile terminal illustrated in FIG. 1.

Referring to FIG. 4, the mobile terminal 130 may provide a second interface 410 for setting the wearing location of the flexible tactile sensor 120. FIG. 4 illustrates an example of an interface which may receive and set the wearing location through a graphic user interface (GUI).

A second interface 410 may include a human body model 420 and receive and set a location where the flexible tactile sensor 120 is worn through the human body model 420. For example, the second interface 410 may receive and set the location where the flexible tactile sensor 120 is worn on the human body model 420 through pointing or dragging. After receiving the location, the second interface 410 may receive the identification number of the corresponding flexible tactile sensor 120.

Referring back to FIG. 1, when the wearing location of the flexible tactile sensor 120 is set, the mobile terminal 130 matches the identification number of at least one flexible tactile sensor 120 with the wearing location of the corresponding sensor in the body of the user and stores the matched identification number and the wearing location in a table.

When the flexible tactile sensor 120 is worn on the body of the user, the mobile terminal 130 receives and stores an initial sensing value from the flexible tactile sensor 120. The initial sensing value may be used to monitor muscle movement or joint bending (e.g., a bending angle, a bending direction, etc.) at the location where the sensor is worn through comparison with the measured sensing value.

When the wearing location of the flexible tactile sensor 120 is set and the initial sensing value is received, the mobile terminal 130 transmits the wearing location and the initial sensing value of the flexible tactile sensor 120 to the monitoring server 140. In an embodiment, the mobile terminal 130 may transmit the table in which the wearing location of the sensor is matched to the monitoring server 140. For example, the mobile terminal 130 may transmit data to the monitoring server using wireless communication means such as a wireless LAN or cellular communication.

When the initial setting and initial value measurement procedures are terminated, the mobile terminal 130 transmits the sensing value received from each flexible tactile sensor 120 to the monitoring server 140. In an embodiment, the mobile terminal 130 may transmit the sensing value received from the flexible tactile sensor 120 and the identification number in the sensor to the monitoring server 140. In another embodiment, the mobile terminal 130 may transmit the sensing value received from the flexible tactile sensor 120 and information where the sensor is worn to the monitoring server 140.

The monitoring server 140 analyzes the movement of the user's muscle or the bending (e.g., the bending angle, the bending direction, etc.) of the joint based on the sensing value measured by the flexible tactile sensor 120 and monitors motility of the user 110.

In an embodiment, when the user's movement monitoring system is used to monitor the remedial exercise of the user, the monitoring server 140 may monitor a result of the remedial exercise of the user 110 based on the received sensing value. For example, the monitoring server 140 may monitor the degree of improvement of the muscular movement of the user 110 or the bending (e.g., the bending angle, the bending direction, etc.) of the joint depending on the remedial exercise. For example, the monitoring server 140 compares a past analysis result (or sensing value) of the user 110 with a current analysis result (or sensing value) to analyze the degree of improvement of the movement of the muscle or a functional improvement degree of the joint and monitor an effect of the remedial exercise.

In an embodiment, when the user movement monitoring system is used to monitor training of the user, the monitoring server 140 may monitor a training result of the user 110 based on the received sensing value. For example, the monitoring server 140 may monitor 140 may compare a reference posture of the training exercise and a posture of the user 110 depending on the movement of muscle or the bending (e.g., the bending angle, the bending direction, etc.) of the joint of the user 110 and monitor a comparison result. For example, the monitoring server 140 compares a past analysis result (or sensing value) of the user 110 with a current analysis result (or sensing value) to analyze the degree of accuracy improvement of the posture and the effect of the training.

In an embodiment, the monitoring server may provide monitoring result information to the mobile terminal 130. In another embodiment, the monitoring server 140 may provide the monitoring result information to a terminal (not illustrated) of a medical team.

Figure 5:
FIG. 5 is a block diagram illustrating a configuration of the flexible tactile sensor illustrated in FIG. 1.

FIG. 5 is a block diagram illustrating a configuration of the flexible tactile sensor illustrated in FIG. 1.

Referring to FIG. 5, the flexible tactile sensor 120 includes a tactile sensor array 510 including a plurality of tactile sensor modules and a communication unit 520 transmitting a sensing value output from the tactile sensor array 510 wirelessly or by wire.

For example, the communication unit 520 may transmit the sensing value to the mobile terminal 130 using a wireless communication means such as Bluetooth, wireless LAN, or short-range wireless communication.

Figure 6:
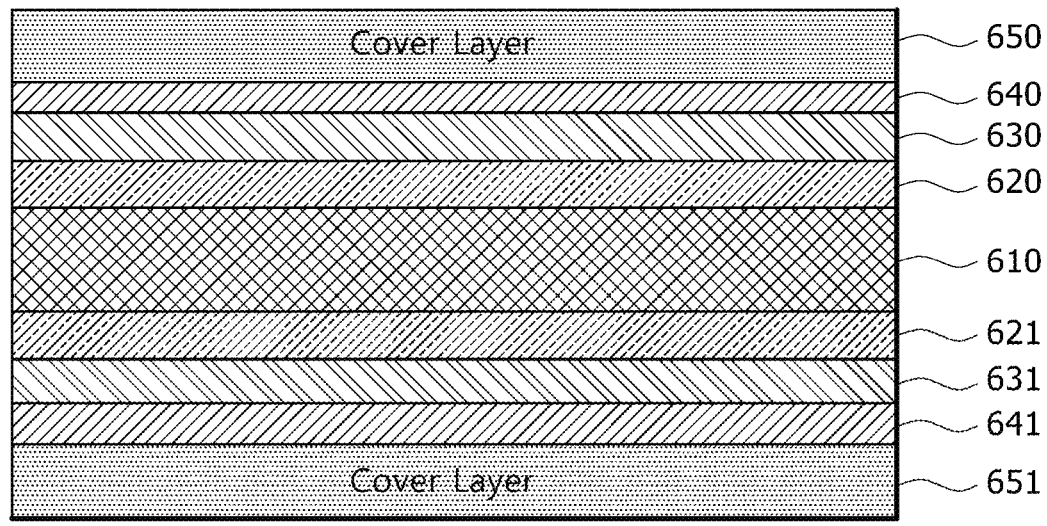
FIG. 6 is a schematic cross-sectional view of a tactile sensor module included in the flexile tactile sensor illustrated in FIG. 5.

FIG. 6 is a schematic cross-sectional view of a tactile sensor module included in the flexile tactile sensor illustrated in FIG. 5.

Referring to FIG. 6, the flexible tactile sensor module is constituted by a polymer layer 610, a first metal layer 620 formed on the top of the polymer layer 610, a first sensor layer 630 including a strain gauge formed on the top of the first metal layer 620 and having a resistance value which varies depending on strain and a metal wire connected to the strain gauge, a first cover layer 650 protecting the first sensor layer 630, a second metal layer 621 formed on the bottom of the polymer layer 610, a second sensor layer 631 including the strain gauge formed on the bottom of the second metal layer 621 and having the resistance value which varies depending on strain and the metal wire connected to the strain gauge, and a second cover layer 651 protecting the second sensor layer 631.

The polymer layer 610 may be flexibly bent to external force while maintaining a structure of a sensor. In an embodiment, the polymer layer 610 may be a polyimide (PI) layer. Polyimide has high thermal stability, stable physical and chemical properties, is thin, and has excellent flexibility. In an embodiment, the polymer layer 610 may be formed with a thickness of 25 μm.

The first metal layer 620 and the second metal layer 621 are formed on the top (alternatively, outward) and the bottom (alternatively, outward) of the polymer layer 610, respectively. The first metal layer 620 and the second metal layer 621 may be formed by depositing nickel-chromium (Ni—Cr) on the upper and lower parts of the polymer layer 610. In an embodiment, each of the first metal layer 620 and the second metal layer 621 may be formed with a thickness of 400 ÅA. In an embodiment, the first metal layer 620 and the second metal layer 621 may be deposited only at a location where the strain gauge is to be patterned.

The first sensor layer 630 includes the strain gauge formed above the first metal layer 620 and having the resistance value which varies depending on the strain and the metal wire connected to the strain gauge. The strain gauge may be patterned on the top of the first metal layer 620 and thereafter, the metal wire may be connected to the strain gauge. The metal wires are connected to one end and the other end of the strain gauge, respectively to be connected to the first and second electrodes. The metal wire is patterned with copper (Cu) to be connected to the strain gauge. In an embodiment, the first sensor layer 630 may be formed with a thickness of 13 μm.

The second sensor layer 631 includes the strain gauge formed on the bottom of the second metal layer 621 and having the resistance value which varies depending on the strain and the metal wire connected to the strain gauge. A description of the second sensor layer 631 is the same as that of the first sensor layer 630.

The first cover layer 650 protecting the first sensor layer 630 may be formed on top of the first sensor layer 630 and the second cover layer 651 protecting the second sensor layer 631 may be formed on the bottom of the second sensor layer 631. In an embodiment, the cover layers 650 and 651 may be polyester (PET) layers.

A first adhesive layer 640 may be formed on the top of the first sensor layer 630 and the first cover layer 650 may be bonded to the top of the first sensor layer 630 through the first adhesive layer 640. Similarly, a second adhesive layer 641 may be formed on the bottom of the second sensor layer 631 and the second cover layer 651 may be bonded to the bottom of the second sensor layer 631 through the second adhesive layer 641. For example, the cover layers 650 and 651 may be bonded after applying an adhesive to the sensor layers 630 and 631 or attaching an adhesive film.

The flexible tactile sensor of FIG. 6 is equipped with sensors on both surfaces to sense force on both surfaces. For example, when the flexible tactile sensor is bent to one side by external force, bending the flexible tactile sensor may be sensed on both surfaces (bending up and bending down), thereby increasing accuracy of the sensing. Further, the flexible tactile sensor may measure normal force applied to one point of the corresponding tactile sensor.

Figure 7:
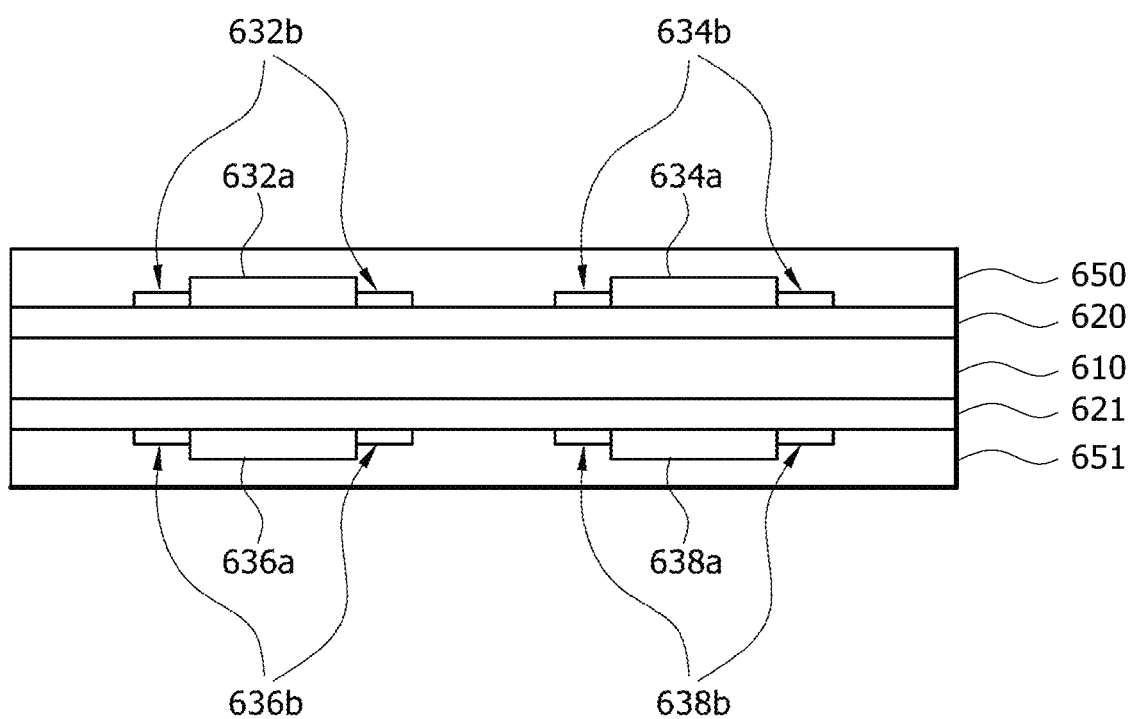
FIG. 7 is a specific cross-sectional view of the tactile sensor module illustrated in FIG. 6.

FIG. 7 is a specific cross-sectional view of the tactile sensor module illustrated in FIG. 6.

Referring to FIG. 7, the first sensor layer 630 includes a first strain gauge 632a, a first metal wire 632b connected to each of one end and the other end of the first strain gauge 632a, a second strain gauge 634a, and a second metal wire 634b connected to each of one end and the other end of the second strain gauge 634a. The first strain gauge 632a and the second strain gauge 634a may be formed to be spaced apart from each other.

In an embodiment, the first strain gauge 632a and the first metal wire 632b may correspond to driving sensor modules and the second strain gauge 634a and the second metal wire 634b may correspond to correction sensor modules. For example, the first strain gauge 632a may output a first sensing value via the first metal wire 632b and output a second sensing value for correcting the first sensing value through the second metal wire 634b.

For example, a metal strain gauge may have a resistance characteristic that resistance linearly increases as a temperature rises. Accordingly, the monitoring server includes a module or algorithm for correcting the sensing value, and the monitoring server may correct an error of the sensing value by a temperature difference between the sensor modules by using the first sensing value output from the driving sensor module and the second sensing value output from the correction sensor module.

The second sensor layer 632 includes a third strain gauge 636a, a third metal wire 636b connected to each of one end and the other end of the third strain gauge 636a, a fourth strain gauge 638a, and a fourth metal wire 638b connected to each of one end and the other end of the fourth strain gauge 638a. The third strain gauge 636a and the fourth strain gauge 638a may be formed to be spaced apart from each other.

In an embodiment, the third strain gauge 636a and the third metal wire 636b may correspond to the driving sensor modules and the fourth strain gauge 638a and the fourth metal wire 638b may correspond to the correction sensor modules. For example, the third strain gauge 636a may output a third sensing value through the first metal wire 636b and the fourth strain gauge 638a may output a fourth sensing value for correcting the third sensing value through the fourth metal wire 638b.

In an embodiment, the first metal layer and the second metal layer may be deposited over the polymer layer 610 and may be deposited only at locations 620a, 620b, 621a, and 621b where the strain gauge is patterned.

Figure 8:
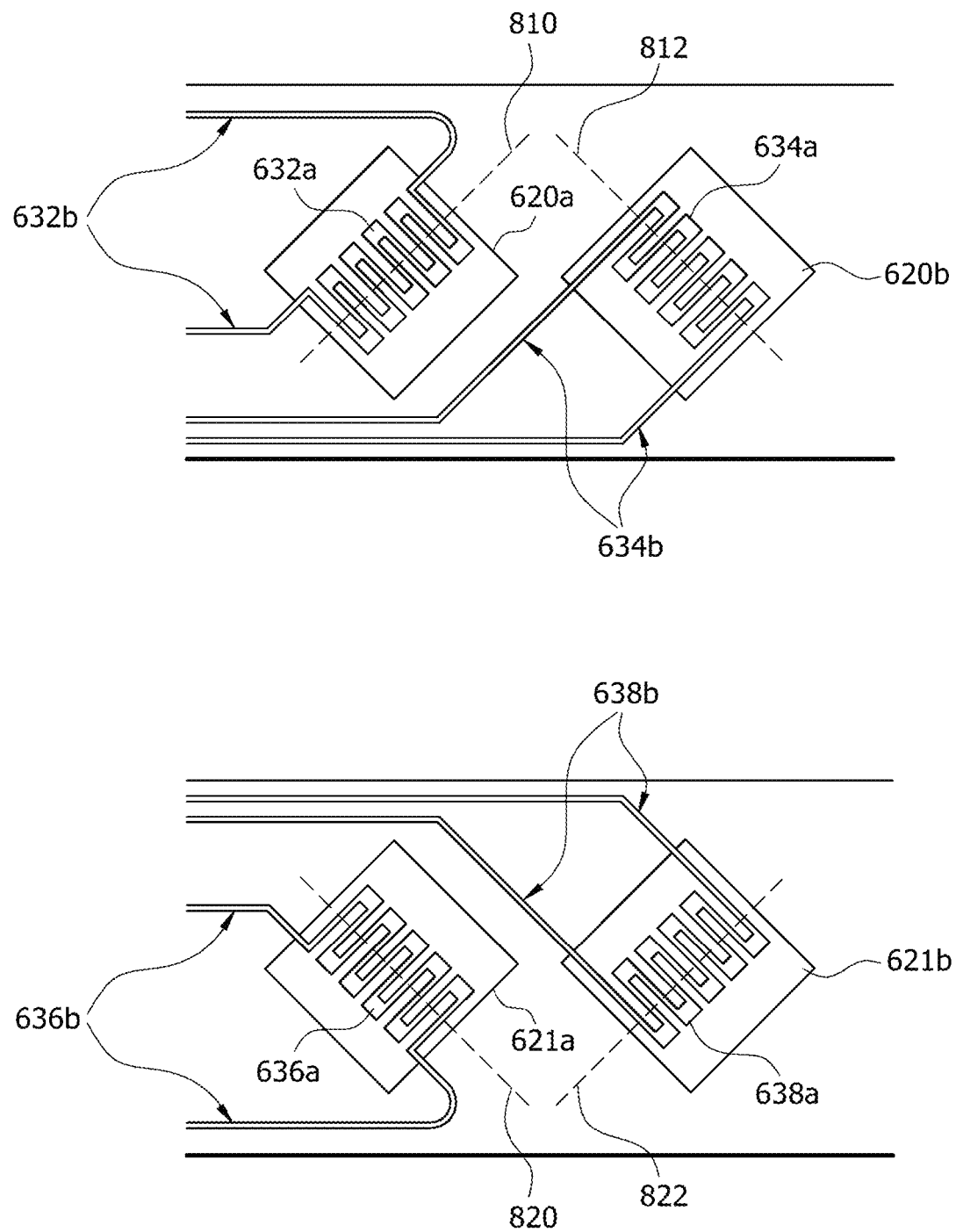
FIG. 8 is a diagram for describing a strain gauge and a metal wire of the tactile sensor module illustrated in FIG. 7.

FIG. 8 is a diagram for describing a strain gauge and a metal wire of the tactile sensor module illustrated in FIG. 7.

Referring to FIG. 8, the strain gauges 632a, 634a, 636a, and 638a may be patterned in a continuous 'ㄹ' shape. Each metal wire may be connected to the end of each strain gauge.

In an embodiment, lengths of line widths and lengths of gaps between lines of the strain gauges 632a and 636a of the driving sensor module and the strain gauges 634a and 638a of the correction sensor module may be different from each other. The length of the line width and the length of the gap between the lines may be implemented to be different according to an application target of the sensor or a main measurement direction of the force.

For example, a width of lines (line patterns) of the strain gauges 632a and 636a of the driving sensor module may be in a range of 40 μm to 90 μm, a gap between two immediately neighboring lines (line patterns) may be in a range of 110 μm to 160 μm, a width of lines of the strain gauges 634a and 638a of the correction sensor module may be in a range of 50 μm to 100 μm, a gap between the two immediately neighboring lines may be 100 μm to 150 μm.

In an embodiment, a width of lines (line patterns) the strain gauges 632a and 636a of the driving sensor module is 65 μm, the length of a gap between two immediately neighboring lines is 135 μm, a width of lines of the strain gauges 634a and 638a of the correction sensor module is 75 μm, and a gap between the two immediately neighboring lines is 125 μm.

In an embodiment, the strain gauges 632a, 634a, 636a, and 638a may be formed in a direction to easily measure the bending force or the normal force. For example, the strain gauges 632a, 634a, 636a, and 638a may be formed such that at least a portion (e.g., top and bottom portions) of an expected folding line or bending line of the flexible tactile sensor becomes parallel to longitudinal axes 810, 812, 820, and 822 of the strain gauges 632a, 634a, 636a, and 638a. As the folding line or bending line of the flexible tactile sensor becomes parallel to the longitudinal axes 810, 812, 820, and 822 of the strain gauges 632a, 634a, 636a, and 638a, strain rate of the strain gauge becomes larger and measurement accuracy may be thus increased. In an embodiment, the expected folding line or bending line of the flexible tactile sensor is assumed by a designer in advance by considering an application target, an application location, or force to be measured and the strain gauges 632a, 634a, 636a, and 638a may be formed based on the assumption. For example, in FIG. 8, the first strain gauge 632a of the driving sensor module and the second strain gauge 634a of the correction sensor module may be formed such that each of the longitudinal axes 810 and 812 has a predetermined angle with a vertical axis of a plane (the axes 810 and 812 have different orientations when viewed over the top, in a direction perpendicular to a major surface of the polymer layer). For example, the first strain gauge 632a and the second strain gauge 634a is formed to be oblique to each other.

In an embodiment, the first strain gauge 632a and the second strain gauge 634a are spaced apart from each other and the respective longitudinal axes 810 and 812 cross each other to be formed to have a shape of '/\'.

The third strain gauge 636a of the driving sensor module and the fourth strain gauge 638a of the correction sensor module may be formed such that each of the longitudinal axes 820 and 822 has a predetermined angle with the vertical axis of the plane. For example, the third strain gauge 636a and the fourth strain gauge 638a may be formed to be oblique to each other.

In an embodiment, the third strain gauge 636a and the fourth strain gauge 638a are spaced apart from each other and the respective longitudinal axes 820 and 822 cross each other to be formed to have the shape of '\/'.

In an embodiment, the first strain gauge 632a and the third strain gauge 636a may be formed at opposite locations corresponding to each other and the second strain gauge 634a and the fourth strain gauge 638a may be formed at opposite locations corresponding to each other. In another embodiment, the first strain gauge 632a and the second strain gauge 634a at one side and the third strain gauge 636a and the fourth strain gauge 638a may be formed to cross each other (to have different orientations when viewed in a direction perpendicular to a major surface of the polymer layer). For example, the first strain gauge 632a, the third strain gauge 636a, the second strain gauge 634a, and the fourth strain gauge 638a may be formed to cross each other in order.

In the flexible tactile sensor configured as above, the sensors are provided on both surfaces to accurately sense the force on both surfaces.

Figure 9:
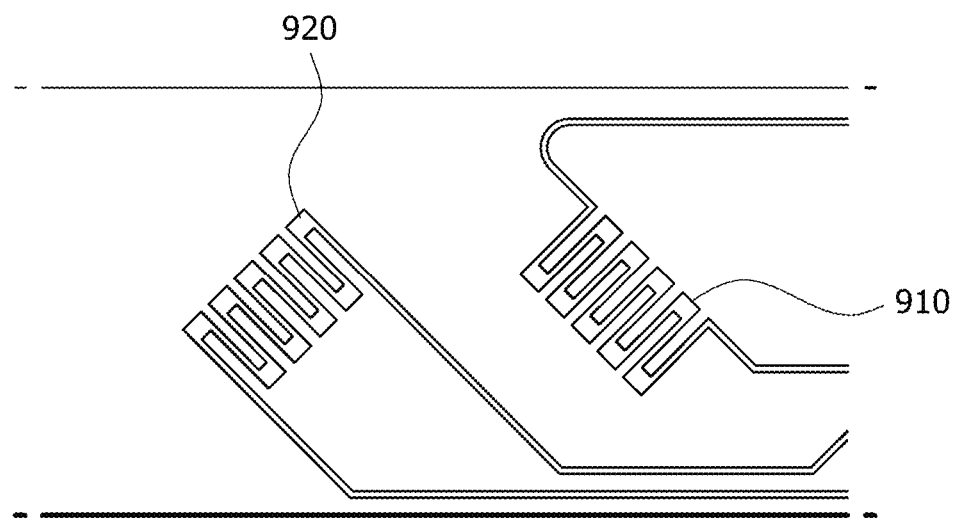
FIG. 9 is a diagram illustrating an implementation example of the tactile sensor module illustrated in FIG. 7.

FIG. 9 is a diagram illustrating an implementation example of the tactile sensor module illustrated in FIG. 7.

Referring to FIG. 9, it can be seen that a driving sensor module 910 and a correction sensor module 920 are formed on one side of the flexible tactile sensor. The strain gauges of the tactile sensor module may be formed on the same surface or on different surfaces as illustrated in FIG. 9.

Figure 10A:
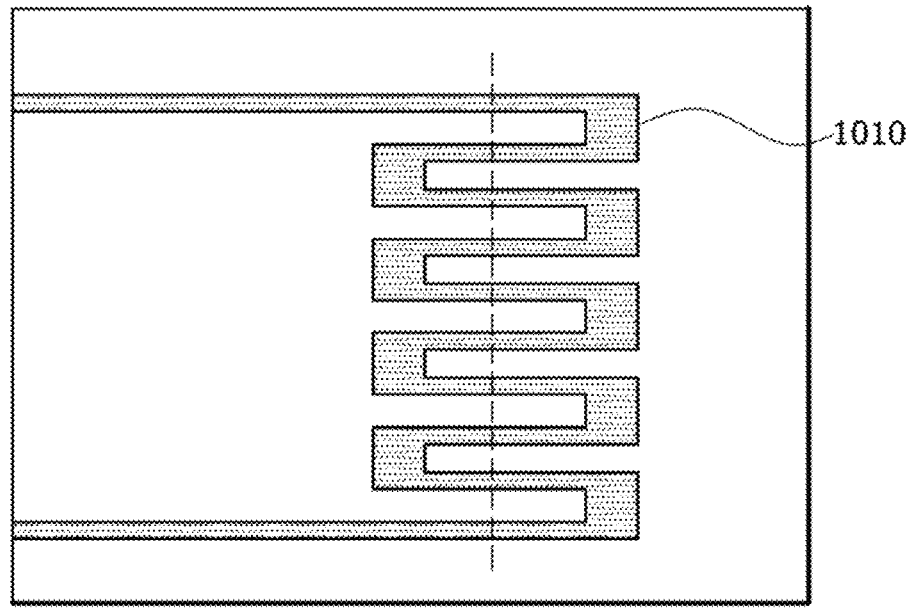
FIGS. 10A and 10B illustrate another implementation example of the tactile sensor module.
Figure 10B:
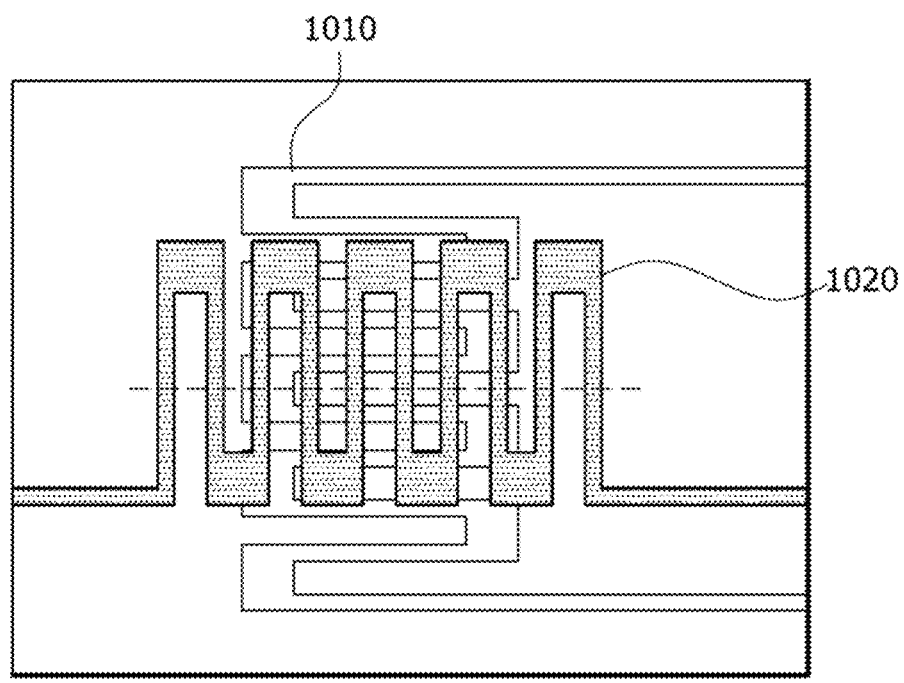

FIGS. 10A and 10B illustrate another implementation example of the tactile sensor module.

The first strain gauge 1010 may be formed on a first surface (FIG. 10A) and a second strain gauge 1020 may be formed on a second surface (an opposite surface of the first surface) (FIG. 10B). In an embodiment, the first strain gauge 1010 and the second strain gauge 1020 may be formed such that the respective longitudinal axes are perpendicular to each other. In another embodiment, the first strain gauge 1010 and the second strain gauge 1020 may be formed such that the respective longitudinal axes are cross obliquely to each other.

For example, in FIGS. 10A and 10B, the first strain gauge 1010 may be formed such that the longitudinal axis is perpendicular to a horizontal plane of the first surface (FIG. 10A) and the second strain gauge 1020 may be formed such that the longitudinal axis is parallel to the horizontal plane of the second surface (FIG. 10B) and perpendicular to each other. Through the tactile sensor module formed as described above, a user may confirm a strain direction according to applied force.

In an embodiment, the first strain gauge 1010 may correspond to the strain gauge of the first driving sensor module and the second strain gauge 1020 may correspond to the strain gauge of the second driving sensor module. In this case, the monitoring server may include a module or algorithm for correcting the sensing value in a predetermined manner and may correct the sensing value output from each driving sensor module.

In another embodiment, the first strain gauge 1010 may correspond to the strain gauge of the driving sensor module and the second strain gauge 1020 may correspond to the strain gauge of the correction sensor module.

Figure 11:
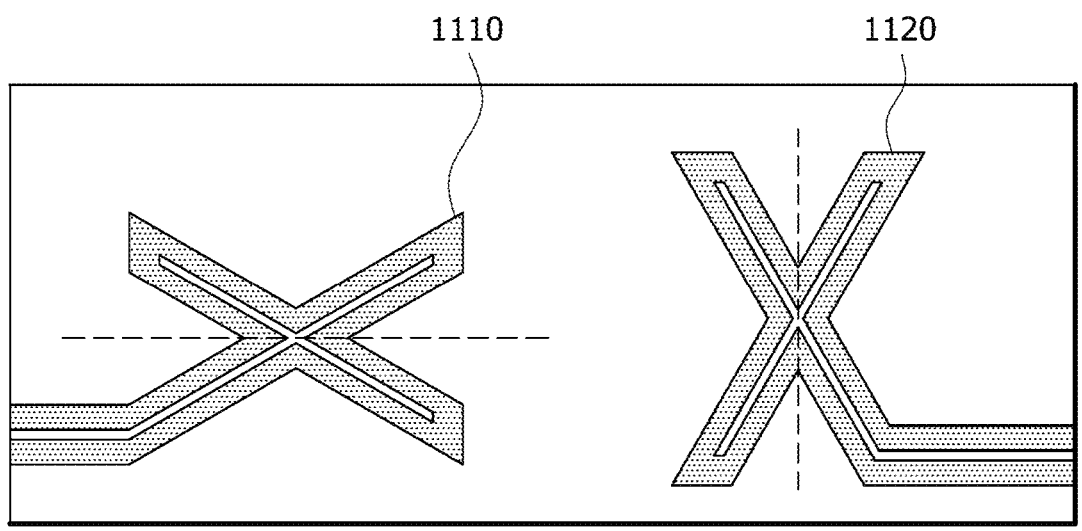
FIG. 11 is a diagram illustrating yet another implementation example of the tactile sensor module.

FIG. 11 is a diagram illustrating yet another implementation example of the tactile sensor module.

Referring to FIG. 11, a first strain gauge 1110 and a second strain gauge 1120 may be formed on the same plane. In another embodiment, the first strain gauge 1110 and the second strain gauge 1120 may be formed on different surfaces.

Each of the strain gauges 1110 and 1120 may be patterned in an 'X' shape and metal wires may be connected to ends of the strain gages 1110 and 1120, respectively.

In an embodiment, the longitudinal axis of the first strain gauge 1110 and the longitudinal axis of the second strain gauge 1120 may be formed to be different directions. For example, in FIGS. 10A and 10B, the first strain gauge 1110 may be formed such that the longitudinal axis is parallel to the horizontal plane of the corresponding surface and the second strain gauge 1120 may be formed such that the longitudinal axis is perpendicular to the horizontal surface of the corresponding surface. In another embodiment, the longitudinal axis of the first strain gauge 1110 and the longitudinal axis of the second strain gauge 1120 may be formed to be the same direction.

In an embodiment, the first strain gauge 1110 may correspond to the strain gauge of the first driving sensor module and the second strain gauge 1120 may correspond to the strain gauge of the second driving sensor module. In this case, the monitoring server (or the manager) may include a module or algorithm for correcting the sensing value in a predetermined manner and may correct the sensing value output from each driving sensor module.

In another embodiment, the first strain gauge 1110 may correspond to the strain gauge of the driving sensor module and the second strain gauge 1120 may correspond to the strain gauge of the correction sensor module.

In the embodiments of FIGS. 9 to 11, each flexible tactile sensor includes strain gauges of the same pattern, but one flexible tactile sensor may include strain gauges of different patterns. For example, one flexible tactile sensor may include both a strain gauge of a continuous 'ㄹ' shape and a strain gauge having an 'X' shape.

Figure 12:
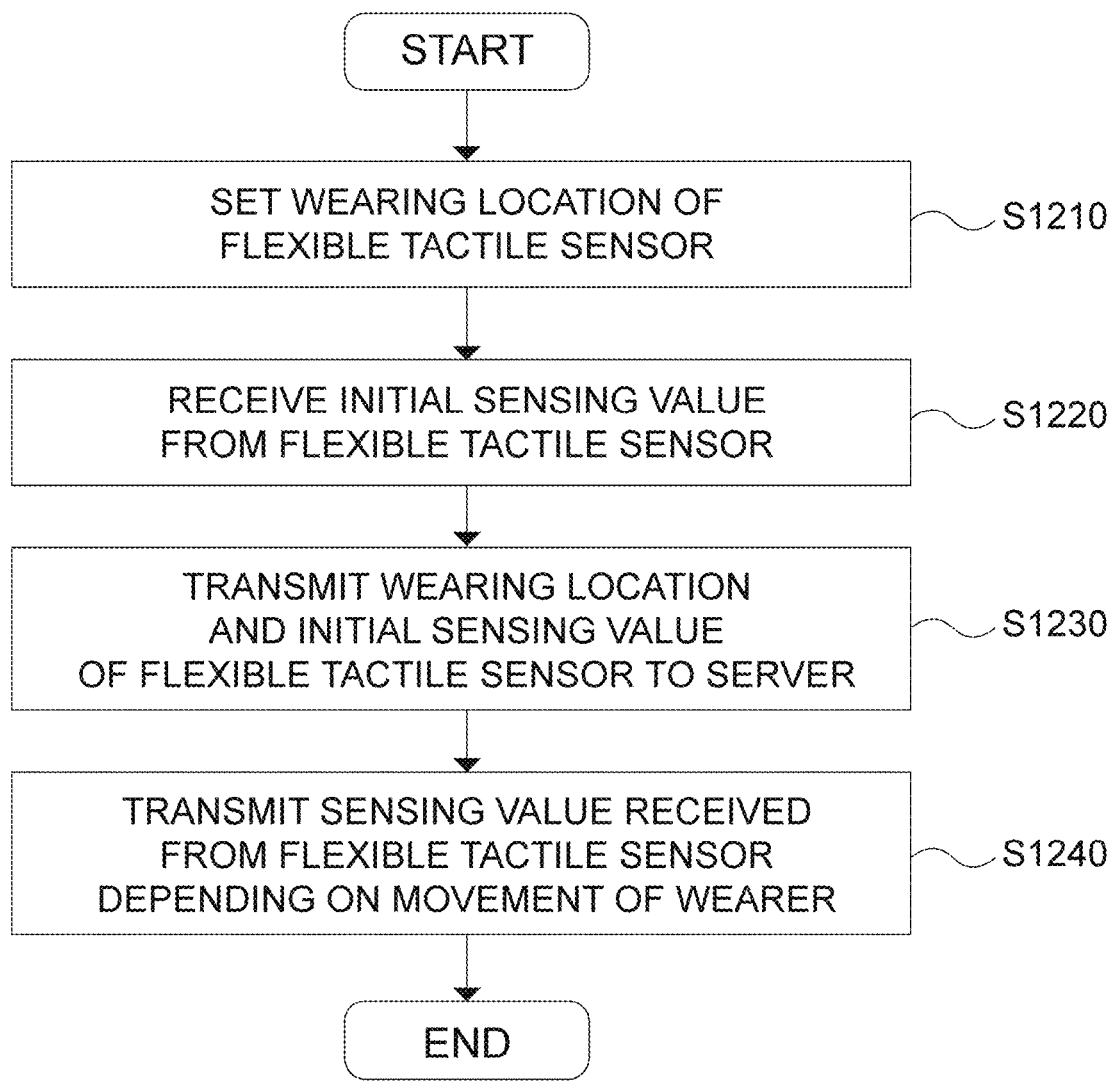
FIG. 12 is a flowchart for describing some processes of a method for monitoring a user state, which is performed by the mobile terminal illustrated in FIG. 1.

FIG. 12 is a flowchart for describing some processes of a method for monitoring a user state, which is performed by the mobile terminal illustrated in FIG. 1.

Referring to FIG. 12, the mobile terminal 130 may perform initial setting and initial value measurement procedures under the control of the user.

At least one flexible tactile sensor 120 may be worn on the body of the user 110 and the flexible tactile sensor senses the movement of the muscle or the bending of the joint at a location where the sensor is worn. The flexible tactile sensor 120 senses force on both planes to accurately sense the movement of the muscle or bending of the joint. The flexible tactile sensor includes a sensor array constituted by the tactile sensor module and a communication unit. The tactile sensor module may have a structure described in FIGS. 5 to 9.

The mobile terminal 130 sets the wearing location of the flexible tactile sensor under the control of the user (step S1210). The mobile terminal 130 matches the identification number of at least one flexible tactile sensor 120 with the wearing location of the corresponding sensor in the body of the user and stores the matched identification number and wearing location in the table.

The mobile terminal 130 receives an initial sensing value from each flexible tactile sensor worn on the body of the user (step S1220). The initial sensing value may be used to monitor muscle movement or joint bending (e.g., a bending angle, a bending direction, etc.) at the location where the sensor is worn through comparison with the measured sensing value measured during the exercise.

The mobile terminal 130 receives the wearing location of the flexible tactile sensor and the initial sensing value to the server (step S1230).

When the initial setting and initial value measurement procedures are terminated, at least one flexible tactile sensor 120 worn on the body of the user senses the movement of the muscle or the bending of the joint at the corresponding location and transmits the sensed values to the mobile terminal 130.

The mobile terminal 130 transmits the sensing value received from the flexible tactile sensor to the monitoring server 140 (step S1240). In an embodiment, the mobile terminal 130 may transmit the sensing value received from the flexible tactile sensor 120 and the identification number in the sensor to the monitoring server 140. In another embodiment, the mobile terminal 130 may transmit the sensing value received from the flexible tactile sensor 120 and information where the sensor is worn to the monitoring server 140.

In an embodiment, the mobile terminal 130 may receive monitoring result information from the monitoring server 140 and display the received result information on the screen.

Figure 13:
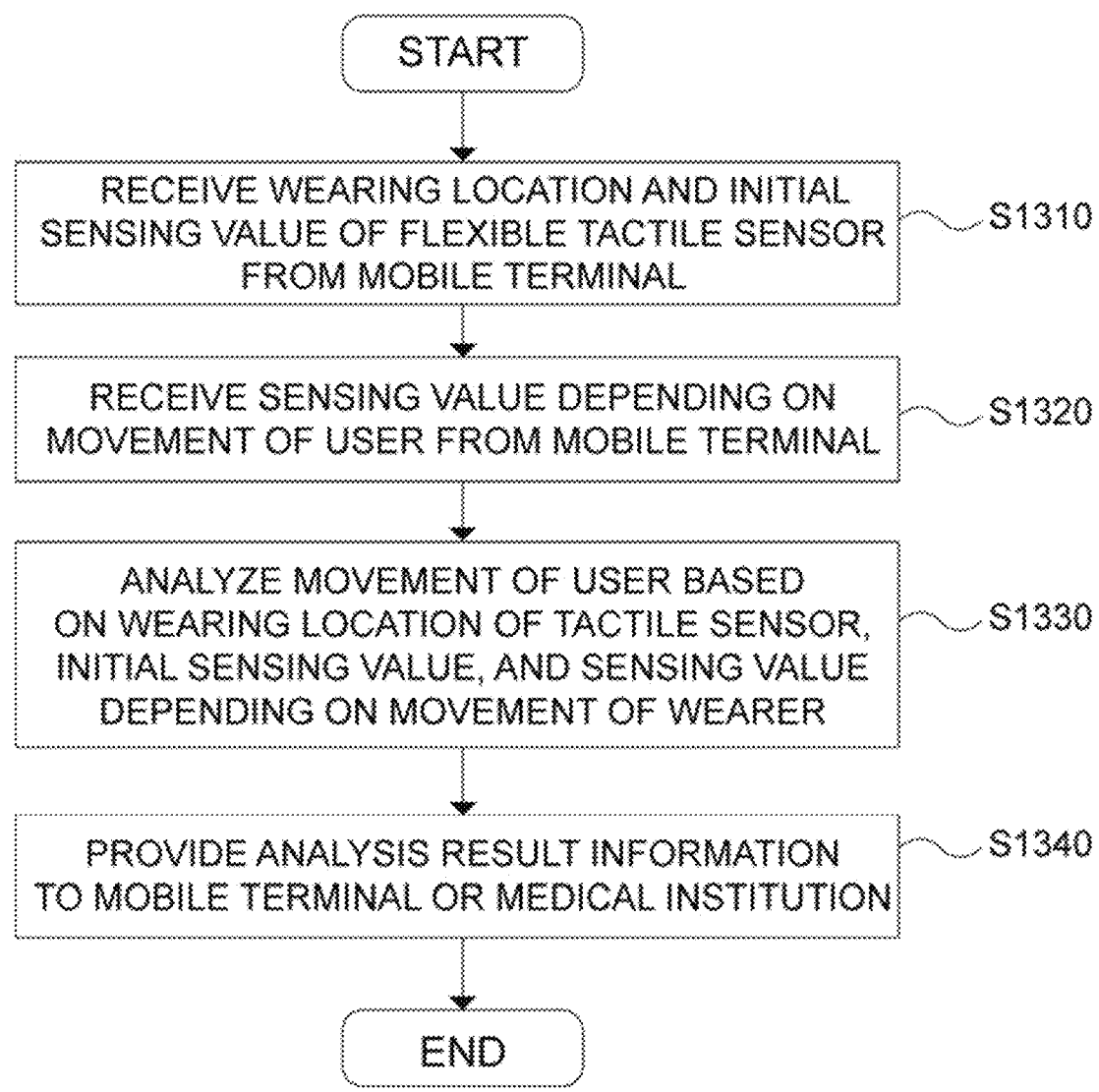
FIG. 13 is a flowchart for describing some processes of a method for monitoring a user state, which is performed by a monitoring server illustrated in FIG. 1.

FIG. 13 is a flowchart for describing some processes of a method for monitoring a user state, which is performed by a monitoring server illustrated in FIG. 1.

Referring to FIG. 13, the monitoring server 140 receives and stores the wearing location and the initial sensing value of the flexible tactile sensor 120 from the mobile terminal 130 (step S1310).

The monitoring server 140 receives the sensing value according to the movement of the user from the mobile terminal 130 (step S1320) and analyzes the movement of the user based on the sensing value according to the wearing location of the tactile sensor, the initial sensing value, and the movement of the wearer (step S1330).

In an embodiment, when the user's movement monitoring system is used to monitor the remedial exercise of the user, the monitoring server 140 may monitor a result of the remedial exercise of the user 110 based on the received sensing value. For example, the monitoring server 140 may monitor the degree of improvement of the muscular movement of the user 110 or the bending (e.g., the bending angle, the bending direction, etc.) of the joint depending on the remedial exercise. The monitoring server 140 compares a past analysis result (or sensing value) of the user 110 with a current analysis result (or sensing value) to analyze the degree of improvement of the movement of the muscle or a functional improvement degree of the joint and monitor an effect of the remedial exercise.

In an embodiment, when the user movement monitoring system is used to monitor training of the user, the monitoring server 140 may monitor a training result of the user 110 based on the received sensing value. For example, the monitoring server 140 may monitor 140 may compare a reference posture of the training exercise and a posture of the user 110 depending on the movement of muscle or the bending (e.g., the bending angle, the bending direction, etc.) of the joint of the user 110 and monitor a comparison result. For example, the monitoring server 140 compares and analyzes a past analysis result (or sensing value) of the user 110 with a current analysis result (or sensing value) to monitor the degree of accuracy improvement of the posture and the effect of the training.

The monitoring server 140 may provide the monitoring result information to the user terminal or the medical team terminal (step S1340). Alternatively, the monitoring server 140 may provide the state monitoring result information to a medical institution server. The medical team terminal may include a terminal owned by a medical team or a terminal provided in a medical institution and may include the PC, the mobile terminal, the tablet PC, or the laptop PC.

The user terminal or the medical team terminal displays the received state monitoring result information on the screen. Logical blocks, modules or units described in connection with embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

The present invention has been described with reference to the preferred embodiments, but those skilled in the art will understand that the present invention can be variously modified and changed without departing from the spirit and the scope of the present invention which are defined in the appended claims.

INDUSTRIAL APPLICABILITY

The present disclosure relates to a technique capable of monitoring a movement of a user, and more particularly, to a method and a system for monitoring a movement of a user, which can accurately sense a movement of a muscle of the user or bending of a joint by using a flexible tactile sensor and monitor a remedial exercise of the user or correcting an exercise posture of the user by using the sensed movement and bending.

What is claimed is:

1. A system for monitoring a movement of a user, the system comprising:
    at least one flexible tactile sensor wearable on a body of the user and configured to sense a movement of a muscle or bending of a joint at a corresponding location of the user and configured to transmit a sensed value; and
    a monitoring server configured to analyze the movement of the muscle or the bending of the joint of the user based on the sensed value received from the at least one flexible tactile sensor and monitor motility of the user,
    wherein the at least one flexible tactile sensor includes a tactile sensor array comprising a plurality of tactile sensor modules, and
    wherein each of the plurality of tactile sensor modules includes:
        a polymer layer,
        a first metal layer formed over the polymer layer,
        a first sensor layer formed over the first metal layer, the first sensor layer comprising a first strain gauge configured to change its resistance based on a first strain and a metal wire connected to the first strain gauge,
        a first cover layer configured to protect the first sensor layer,
        a second metal layer formed under the polymer layer,
        a second sensor layer formed under the second metal layer, the second sensor layer comprising a second strain gauge configured to change its resistance based on a second strain and a metal wire connected to the second strain gauge, and
        a second cover layer configured to protect the second sensor layer.

2. The system of claim 1, further comprising:
    a mobile terminal wirelessly connected with the at least one flexible tactile sensor,
    wherein the mobile terminal is configured to transmit the sensed value received from the at least one flexible tactile sensor to the monitoring server.

3. The system of claim 2, wherein, when the at least one flexible tactile sensor is worn on the body of the user, the mobile terminal is configured to receive and store an initial sensing value of each flexible tactile sensor.

4. The system of claim 2, wherein the mobile terminal includes a table configured to store an identification number of the at least one flexible tactile sensor and a wearing location of a corresponding sensor on the body of the user.

5. The system of claim 1, wherein the at least one flexible tactile sensor is configured to be worn at a location corresponding to a muscle or joint associated with a remedial exercise of the user, and
    wherein the monitoring server is configured to monitor a remedial exercise result of the user based on the received sensed value.

6. The system of claim 5, wherein the monitoring server is configured to monitor an improvement degree of the muscle or a function improvement degree of the joint of the user depending on the remedial exercise.

7. The system of claim 1, wherein the at least one flexible tactile sensor is wearable at a location corresponding to a muscle or joint associated with a training exercise of the user, and wherein the monitoring server is configured to monitor a training exercise result of the user based on the received sensed value.

8. A system for monitoring a movement of a user, the system comprising:
    at least one flexible tactile sensor wearable on a body of the user and configured to sense a movement of a muscle or bending of a joint at a corresponding location of the user,
    wherein the at least one flexible tactile sensor is configured to transmit a sensed value to a monitoring server that is configured to analyze the movement of the muscle or the bending of the joint of the user based on the sensed value and monitor motility of the user,
    wherein the at least one flexible tactile sensor includes a tactile sensor array comprising a plurality of tactile sensor modules, and
    wherein each of the plurality of tactile sensor modules includes:
        a polymer layer,
        a first metal layer formed over the polymer layer,
        a first sensor layer formed over the first metal layer, the first sensor layer comprising a first strain gauge configured to change its resistance based on a first strain and a metal wire connected to the first strain gauge,
        a first cover layer configured to protect the first sensor layer,
        a second metal layer formed under the polymer layer,
        a second sensor layer formed under the second metal layer, the second sensor layer comprising a second strain gauge configured to change its resistance based on a second strain and a metal wire connected to the second strain gauge, and
        a second cover layer configured to protect the second sensor layer.

9. A method for monitoring a movement of a user, the method comprising:
    sensing, by at least one flexible tactile sensor worn on a body of the user, a movement of a muscle or a bending of a joint at a corresponding location of the user and transmitting a sensed value to a mobile terminal;
    transmitting, by the mobile terminal, the sensed value received from the at least one flexible tactile sensor to a monitoring server; and
    analyzing, by the monitoring server, the movement of the muscle or the bending of the joint of the user based on the sensed value and monitoring motility of the user, wherein the at least one flexible tactile sensor includes a tactile sensor array comprising a plurality of tactile sensor modules, and wherein each of the plurality of tactile sensor modules includes:
- a polymer layer,
- a first metal layer formed over the polymer layer,
- a first sensor layer formed over the first metal layer, the first sensor layer comprising a first strain gauge configured to change its resistance based on a first strain and a metal wire connected to the first strain gauge,
- a first cover layer configured to protect the first sensor layer,
- a second metal layer formed under the polymer layer,
- a second sensor layer formed under the second metal layer, the second sensor layer comprising a second strain gauge configured to change its resistance based on a second strain and a metal wire connected to the second strain gauge, and
- a second cover layer configured to protect the second sensor layer.

\* \* \* \* \*